United States Patent [19]
Fiore et al.

[11] Patent Number: 5,282,382
[45] Date of Patent: Feb. 1, 1994

[54] ROLL HARDNESS OBSERVATION TESTING APPARATUS AND PROCESS

[75] Inventors: Leonard F. Fiore, Foley; Gregory P. Brandl, Holdingford; Allen R. Voit, Sauk Rapids, all of Minn.

[73] Assignee: Champion International Corporation, Stamford, Conn.

[21] Appl. No.: 760,703

[22] Filed: Sep. 16, 1991

[51] Int. Cl.⁵ .......................... G01N 3/48; G01N 3/52
[52] U.S. Cl. ............................................ 73/82; 73/79; 162/198
[58] Field of Search .......................... 73/82, 79, 159, 12, 73/12.01–12.09, 12.11–12.14; 162/263, 198, DIG. 10; 364/507, 560, 561, 562, 563, 561

[56] References Cited

U.S. PATENT DOCUMENTS

| | | | |
|---|---|---|---|
| 2,728,224 | 12/1955 | Wheeler | 73/12 X |
| 3,822,588 | 7/1974 | Knight et al. | 73/81 |
| 4,594,880 | 6/1986 | Murdock et al. | 73/32 R |
| 4,885,933 | 12/1989 | Hiestand et al. | 73/79 |
| 4,888,983 | 12/1989 | Dunfield et al. | 356/448 X |
| 4,966,455 | 10/1990 | Avni et al. | 356/339 X |
| 5,079,728 | 1/1992 | Adams et al. | 73/12 X |

FOREIGN PATENT DOCUMENTS

| | | | |
|---|---|---|---|
| 2558594 | 7/1985 | France | 73/82 |
| 245136 | 10/1987 | Japan | 73/82 |
| 1348737 | 10/1987 | U.S.S.R. | 73/82 |

*Primary Examiner*—Tom Noland

[57] ABSTRACT

An apparatus and process is provided for testing the hardness of paper rolls. The apparatus includes a tester that is selectively moveable across a roll of paper. The tester includes an impact anvil which strikes the paper at a selected frequency and which determines the hardness of the paper roll based on forces encountered by the impact anvil. The tester further includes an encoder wheel for identifying relative positions on the paper roll at which each test is performed. The impact anvil and the encoder wheel are operatively connected to a computer which receives signals and calculates hardness at each of the plurality of positions tested. The computer provides output of data on the most recent traversal of a paper roll and on plural sequentially tested rolls to assess trends in the hardness of paper rolls produced by a particular machine.

3 Claims, 4 Drawing Sheets

ROLL HARDNESS OBSERVATION TESTING APPARATUS AND PROCESS

BACKGROUND OF THE INVENTION

Paper mills include large complex machinery to convert wood pulp into a slurry and subsequently into paper sheets. The paper sheets are wound onto large rolls that may be any size up to six feet in diameter and thirty feet long. A roll of paper produced to these dimensions may weigh up to twenty tons. Some mills may simultaneously produce plural rolls of the same or different axial lengths, with the respective rolls being disposed in generally end-to-end axial alignment. The large rolls of paper generally will be transported to another location for cutting, folding and/or printing in accordance with the intended end use of the paper.

Characteristics of the paper produced by the mill vary widely in accordance with the intended use of the paper. In particular, paper thickness, weight and surface characteristics can vary widely from one specified end use to another.

Many machines are available for testing characteristics of the paper being produced by the mill to ensure that the paper conforms to specifications. For example, available machines will employ samples of the paper being produced to test burst strength, tear strength, thickness, smoothness, gloss and other quantifiable characteristics. A prior art apparatus for determining the density of a finished roll in a mill is shown in U.S. Pat. No. 4,594,880 which issued to Murdoch et al on Jun. 17, 1986. A prior art apparatus for assessing the cross-sectional profile of the paper produced by a mill is shown in U.S. Pat. No. 4,888,983 which issued to Dunfield et al on Dec. 26, 1989. A prior art apparatus for measuring the mottle or surface gloss of paper produced by a mill is shown in U.S. Pat. No. 4,966,455 which issued to Avni et al on Oct. 30, 1990.

It is also desireable to perform non-destructive hardness tests on at least selected rolls produced by a paper mill. In particular, roll hardness observation (rho) meters are employed to test the hardness of a finished roll of paper. The typical prior art rho meter employs a hammer apparatus operatively connected to electronic means, such as an amplifier. The hammer is employed to strike the roll with a specified force, and the response of the hammer after striking the roll is measured and can be compared to specified responses indicative of the roll hardness. The prior art rho meter can be employed at selected locations along the length of the paper roll to accumulate plural readings for assessing hardness.

The prior art rho meters have been large, costly and cumbersome apparatus. Output data of the prior art rho meter has been inaccurate, and it has been difficult to properly correlate the reading taken by the prior art rho meter with the particular location on the paper being tested. Furthermore, the prior art rho meter has not been an effective tool for the anticipation or early identification of problems in the paper mill. A typical prior art rho meter is shown in U.S. Pat. No. 3,822,588 which issued Knight et al on Jul. 9, 1974.

The prior art rho meters do not enable an efficient assessment of roll hardness of paper produced by a mill. Similarly, none of the prior art rho meters provide a simple apparatus that can readily be used by workers at the mill to accurately assess hardness of a roll.

In view of the above, it is an object of the subject invention to provide a rho testing apparatus for accurately and efficiently testing the hardness of a paper roll produced by a mill.

It is another object of the subject invention to provide a rho testing apparatus that is easily transportable by workers in the paper mill.

It is another object of the subject invention to provide a rho testing apparatus and process that accurately correlates hardness data to positions on the roll being tested.

Still a further object of the subject invention is to provide a rho testing apparatus that identifies test positions independent of the speed of moving the rho tester relative to the paper.

Still an additional object of the subject invention is to provide a rho testing apparatus and process for providing the worker with usable information and summaries for assessing the performance of equipment at the paper mill over a selected period of the paper mill operation.

SUMMARY OF THE INVENTION

The subject invention is directed to a roll hardness observation (rho) testing apparatus and method for measuring and analyzing the hardness of a roll of paper produced at a paper mill The rho testing apparatus of the subject invention includes a rho tester moveable along the surface of the paper roll for testing the hardness of the paper roll at a plurality of spaced apart positions thereon. The rho testing apparatus further includes a data acquisition subsystem or computer operatively connected to the rho tester for receiving signals generated by the rho tester and for converting the signals into output data. The rho system may further include output display means, such as a computer monitor and/or a printer operatively connected to the computer for displaying the data received and analyzed by the computer The rho tester of the subject system preferably is of a size, weight and shape conducive to the manual positioning and movement by a worker. For example, the rho tester may weigh less than 12 pounds, and preferably in the range of 8-10 pounds.

The operative parts of the rho tester and any controls and indicators that may be included are mounted to a rho tester housing. The housing may further be provided with handles to enable the worker to carry the rho tester to the paper roll to be tested and to move the rho tester along the paper roll as described herein.

The rho tester may further include power means for ensuring operation of the components of the tester as described below. The power means may include a hard wire extending to an external power source, such as a conventional electrical outlet. Preferably, however, the rho tester includes an internal power source such as a rechargeable and/or replaceable battery pack to minimize the number of wires extending from the rho tester and to enable the rho tester to be used at locations in a manufacturing facility that may be remote from an external power supply.

Traversal means for moving the rho tester across the surface of the paper roll to be tested may be mounted on the housing The traversal means for moving the rho tester may include a plurality of wheels rotatably mounted to the rho tester housing to enable the entire rho tester to be rolled along the surface of the paper roll.

The rho tester further includes hardness measuring means for generating signals indicative of the hardness of the paper roll at each of a plurality of positions. The hardness measuring means may include or cooperate with an impact means that is moveable to periodically impact the surface of the paper roll with a selected force. The hardness measuring means may comprise an accelerometer or other such means for assessing the response of the impact means after each impact. The hardness measuring means may be operatively connected to the computer or data acquisition subsystem, such that electrical signals indicative of the hardness of the paper roll are conveyed from the hardness measuring means to the computer. The rho tester may further include lifting means for lifting the impact means after each impact and peak holding means for preventing the impact means from rebounding at either end of its range of periodic motions.

Position sensing means for identifying the location on the paper roll being tested may be mounted to the rho tester. The position sensing means may be operatively connected to the computer and to the hardness measuring means. In a preferred embodiment, the position sensing means includes an encoder wheel in rolling engagement with the surface of the paper roll being tested. Hardness test results are analyzed and correlated with respect to positions along the surface of the paper roll being tested. The position sensing means and the impact means may both be mounted to the housing of the rho tester for appropriate movement relative thereto. Additionally, the position sensing means and the impact means preferably are in close proximity to one another.

The computer of the subject rho system may receive electrical signals from the hardness measuring means and may calculate hardness data based on the received signals. The computer also may receive signals from the position sensing means for correlating hardness data with position on the roll. The computer may collate and display the calculated hardness data in at least one format. In particular, the computer may calculate and output hardness data at each of a plurality of locations across the width of a single roll. The computer may further calculate and display hardness information for each of a plurality of sequential rolls produced by the paper mill. This latter format of presenting data readily enables the worker to assess trends in hardness from one roll to the next. To further help in the assessment of trends, the computer may calculate averages for selected pluralities of paper rolls. For example, averages for the first several rolls of paper produced by a mill may be compared by the computer to hardness readings for a subsequent plurality of rolls to determine whether the hardness profile has changed during the course of operation of the mill. The output means may be operative to selectively provide the output on either a computer screen or a printer.

DETAILED DESCRIPTION OF THE PREFERRED EMBODIMENT

Figure 1:
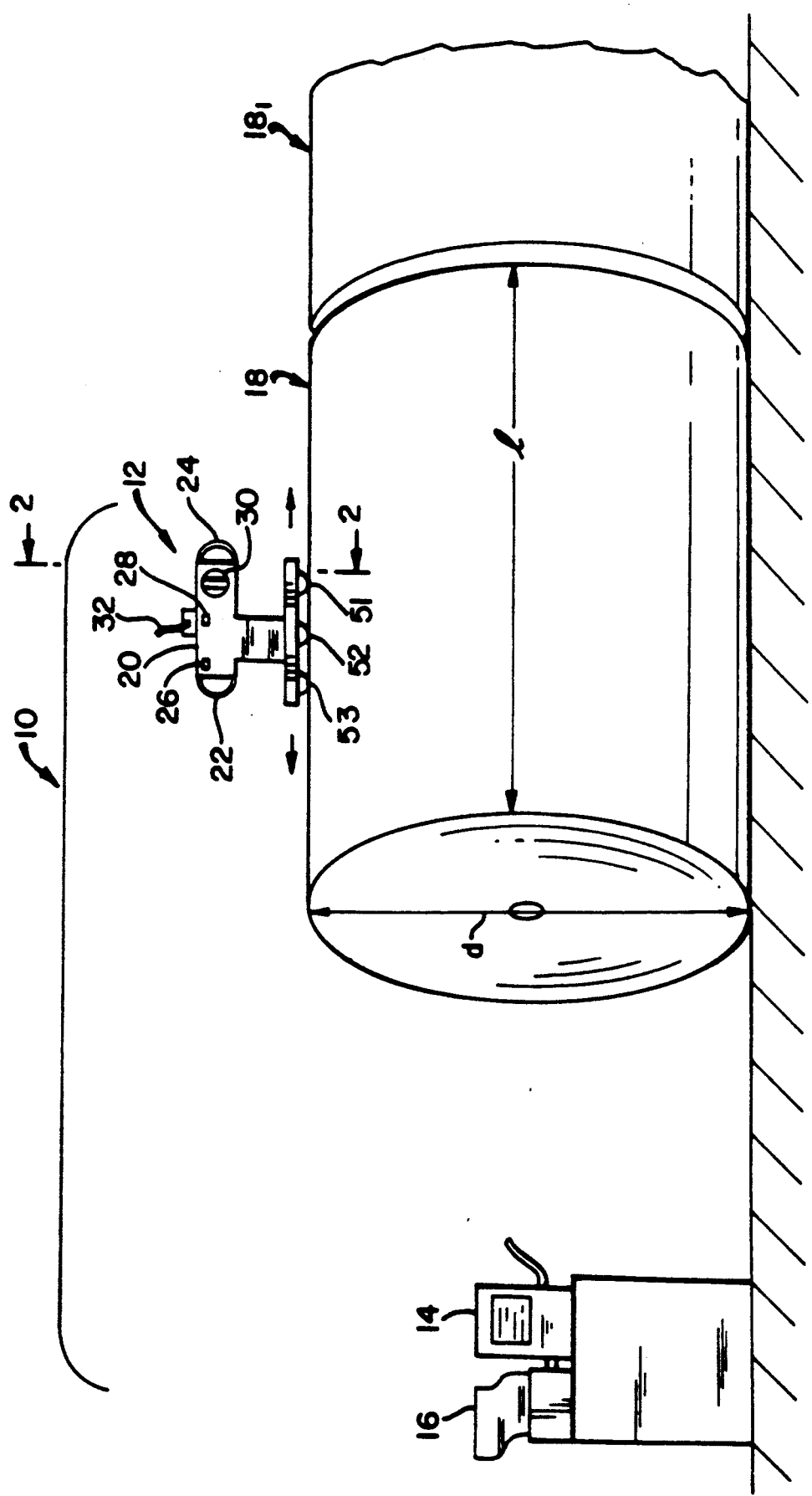
FIG. 1 is a perspective view of the rho testing apparatus of the subject invention.
Figure 2:
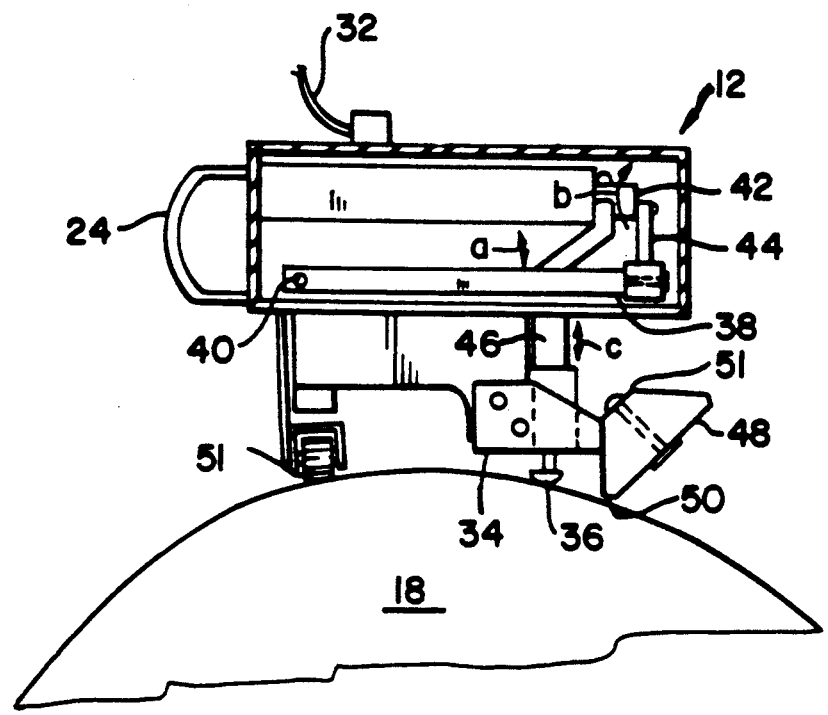
FIG. 2 is a cross-section taken along line 2—2 in FIG. 1.

The rho testing apparatus of the subject invention is identified generally by the numeral 10 in FIG. 1. The apparatus 10 includes a portable rho tester 12, a computer 14 operatively connected to the rho tester 12 and a printer 16 operatively connected to the computer 14. The rho testing apparatus 10 is operative to test the hardness of a paper roll 18. The paper roll 18 is a large heavy roll defining a diameter "d" that may approach six feet and a length "l" that may be up to thirty feet. As noted above, the paper roll 18 of the indicated dimensions may weigh approximately 40,000 pounds. The paper roll 18 depicted in FIGS. 1 and 2 is one of a plurality of such rolls produced sequentially at a paper mill. As will be explained further below, the rho testing apparatus 10 is operative to display trends from one paper roll 18 to the next roll produced sequentially at the paper mill. Additionally, the rho tester 12 of the system 10 is operative to efficiently advance from one roll 18 to another roll $18_1$ axially adjacent thereto or axially aligned but slightly spaced from the roll 18.

The rho tester 12 of the system 10 includes a housing 20 in which the various operative components of the tester 12 are disposed, as explained herein. The housing 20 is provided with handles 22 and 24 on opposed sides thereof to enable the rho tester 12 to be repositioned and efficiently operated by a worker. The housing 20 further includes an externally disposed switch 26 for selectively turning the rho tester 12 on and off. An indicator light 28 is disposed on the housing 20 in proximity to the switch 26 to provide visual indication of when power is supplied to the rho tester 12.

The rho tester 12 further includes a battery pack 30 removably mounted in the housing 20. The battery pack 30 includes at least one rechargeable battery for powering the rho tester 12. A signal cable 32 extends from the tester 12 to the computer 14 for the transmitting electrical signals therebetween.

Figure 3:
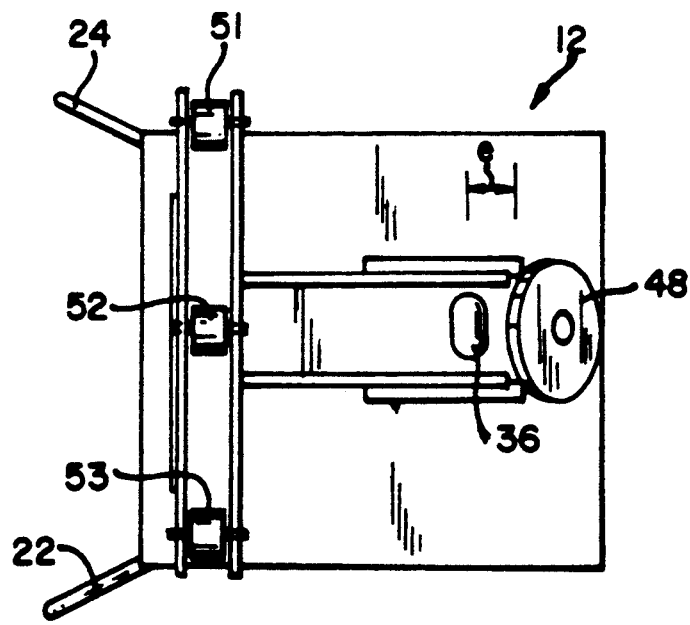
FIG. 3 is a bottom elevational view of the rho tester.

With reference to FIGS. 2 and 3, the tester 12 is provided with a bottom face identified generally by the numeral 34. A striking anvil 36 extends from the bottom face 34 of the tester 12 and is moveable toward and away from the paper roll 18 upon activation of the switch 26. In particular, the striking anvil 36 is rigidly mounted to a lever 38 which in turn is pivotally mounted to the housing 20 at location 40 for pivoting movement in the direction indicated by arrow "a". A rotatable drive member or motor 42 is provided with a drive rod 44 eccentrically and pivotally mounted thereto and pivotally mounted to the lever 38. Thus, the rotation achieved by the drive member 42 as shown by arrow "b" translates into a reciprocating movement of the lever 38 (arrow "a")and the striking anvil 36 as indicated by arrow "c". The motor 42 is operative to achieve 5–20 strikes per second and preferably 15 strikes per second by the anvil 36.

An accelerometer 46 is mounted to the striking anvil 36 for movement therewith. The accelerometer 46 is operative to measure the response of the striking anvil 36 upon each contact with the paper roll 18. In particular, the accelerometer 46 is operative to measure the rebounding characteristics of the striking anvil 36 and to generate electrical signals transmitted by the data cable 32 as an indication of hardness of the paper roll 18.

An encoder wheel 48 is rotatably mounted to the housing 20 in proximity to the striking anvil 36. The encoder wheel 48 is of generally frustoconical configuration, and is disposed such that its major diameter edge 50 is in rolling contact with the paper roll 18 at a location spaced from the striking anvil 36 by a distance "e" which preferably is about 0.5 inch. The close proximity of the encoder wheel 48 with the striking anvil 36 is enabled by the frustoconical configuration of the encoder wheel 48 as depicted in FIG. 2. More particularly, the small diameter edge 51 of the encoder wheel 48 faces upwardly and toward the accelerometer 46. Additionally, the rotational axis of the encoder wheel 48 is aligned at an acute angle to the direction of movement of the striking anvil 36.

The encoder wheel 48 performs two important functions on the rho tester 12. First, the encoder wheel 48 keeps the striking anvil 36 in selected spaced relationship to the paper roll 18 to ensure that the striking anvil 36 will impact the paper roll 18 with a known force. Furthermore, the close proximity of the encoder wheel 48 to the striking anvil 36 ensures that the relative distance of the striking anvil 36 from the paper roll 18 at the top of the trajectory of the striking anvil 36 will be substantially uniform despite differences in the diameter "d" of the rolls 18 being tested.

The second important function carried out by the encoder wheel 48 relates to the relative position of the tester 12 on the paper roll 18. More particularly, the encoder wheel 48 is operatively connected to the computer to transmit signals to the computer indicative of the relative location of the tester 12. Thus, a test of a paper roll 18 begins at one longitudinal end of the roll. The striking anvil 36 impacts the roll 18 at a rate determined by the speed of the motor 42. The rho tester 12 is moved along the roll 18 by the worker at any speed convenient to the worker. The relative position along the roll 18 at which tests are taken by the striking anvil 36 are identified by the signals generated by the encoder wheel 48 which rolls along the surface of the paper roll 18 as tests are being performed. Thus, the computer 14 receives two signals, namely, a first set of signals from the accelerometer 46 to indicate the hardness of the paper roll 18, and a second set of signals from the encoder wheel 48 to indicate the relative position on the paper roll 18 at which the hardness is being measured.

The rho tester 12 further includes a plurality of support wheels 51, 52 and 53 disposed in a linear array generally adjacent the rear side of the tester 12. The support wheels 51-53 cooperate with the encoder wheel 48 to ensure that the striking anvil 36 is properly positioned with respect to the surface of the paper roll 18. The wheels 51-53 enable the rolling movement of the tester along the surface of the paper roll 18. The spaced apart disposition of the respective wheels 51-53 ensure that the tester 12 is properly supported at all locations along the paper roll 18 even at locations in very close proximity to the ends of the roll 18. Thus, accurate readings can be taken entirely along the paper roll 18 from one longitudinal end to the other. Additionally, the position of the rolls 51-53 efficiently enables tests to be carried out along rolls that are disposed in generally end-to-end orientation or slightly spaced axial alignment relative to one another.

Figure 4A:
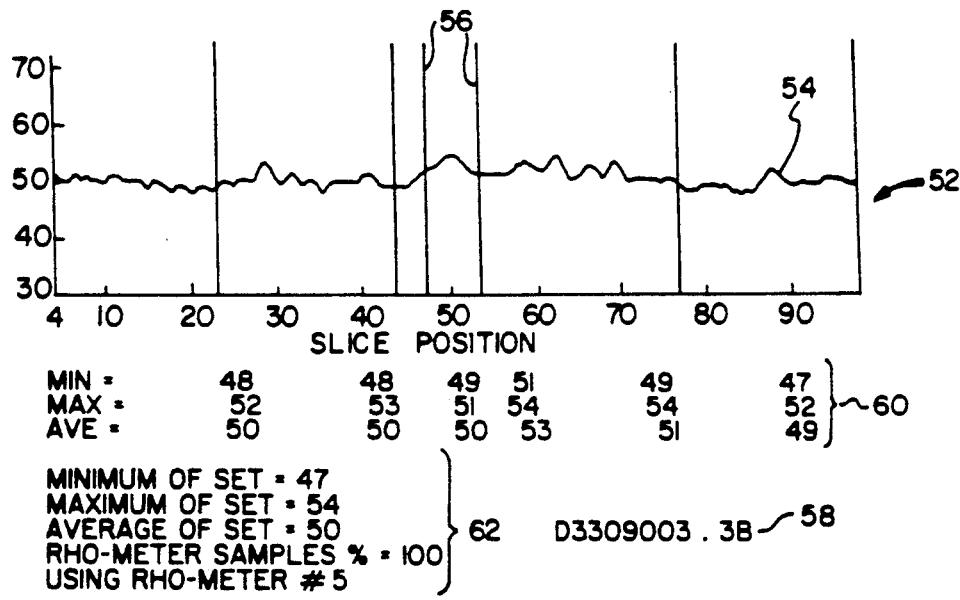
FIGS. 4a–4c illustrate the output data produced by the monitor and printer of the subject rho testing apparatus.
Figure 4B:
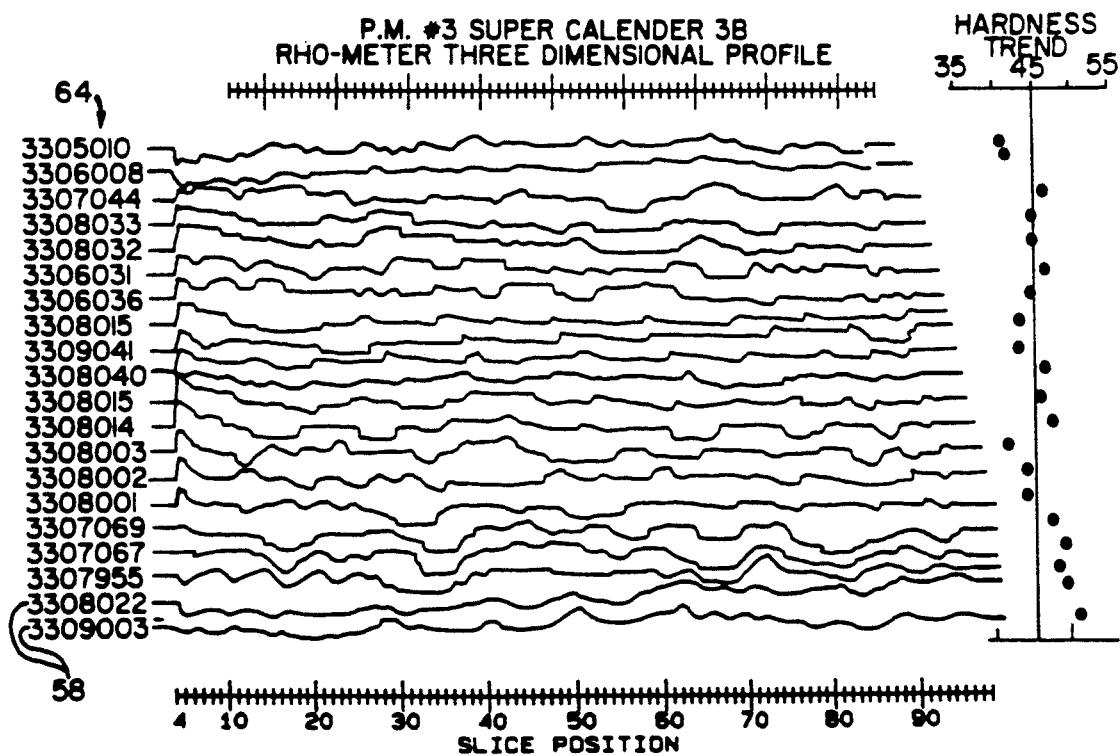
Figure 4C:
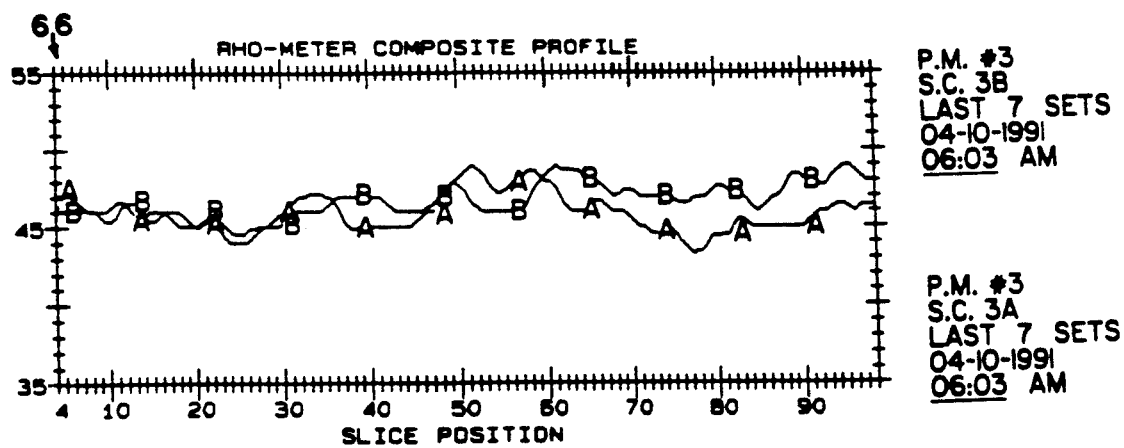

The signals generated by the accelerometer 46 and the encoder wheel 48 are received by the computer 14 and are analyzed to determine hardness at each of plural positions along the length of the paper roll 18. The calculated hardness is then displayed by the screen 15 on the computer 14 and/or by the printer 16 operatively connected to the computer 14. FIGS. 4a–4c illustrate a typical output from the computer screen 15 and/or the printer 16. In particular, the output shown in FIG. 4a includes a graph 52 with an irregular generally horizontal line 54 to indicate the hardness at each of plural positions along the length of a plurality of axially arrayed rolls, such as the rolls 18 and $18_1$. The demarcation between adjacent rolls is identified by the vertical lines 56. The computer further identifies the particular traversal across the roll 18 or across a plurality of end-to-end rolls 18, $18_1$ by an assigned identification number 58. Calculations then are performed and printed for the most recent traversal. In particular, the array of calculations identified generally by the numeral 60 in FIG. 4a provides the minimum hardness reading, the maximum hardness reading and the average for each of the axially aligned rolls 18, $18_1$ being tested. The data identified by the numeral 62 identifies the minimum, maximum and average for the entire set of tests performed on the traversal depicted by the graph 52. The data 62 further indicates the percentage of the set that was actually tested by the rho tester 12. In particular, exceptionally high readings or exceptionally low readings could be disregarded based upon input parameters provided to the computer for cut positions. The data 62 further identifies the particular rho tester 12 being employed.

The computer further provides an array of data identified generally by the numeral 64 in FIG. 4b. In particular, the data 64 shows the output provided by each of a plurality of sequentially performed traversals of the paper rolls 18. It will be noted that test identification numbers are presented in the left hand margin of the outputed data 64. The central portions of the outputed data 64 shows an array of graphs similar to the horizontal line 54 in the graph 52. The right hand side of the data array 64 shows trends in the average hardness for each test. Additionally, by viewing any particular vertical line or slice position across the array of data 64, trends at particular axial locations of rolls produced by a paper machine can be examined. This information can be used to make adjustments in the paper mill equipment to achieve greater uniformity of hardness.

A summary data array 66 is provided in the bottom portion of the output illustrated in FIG. 4c. Lines A and B in graph 66 show an average of the last seven profiles tested from two machines A and B. It will be noted that the range is very close on the left side of the graph 66. However, the range widens in the right half. This widening of the range may be indicative of problems in the portion of the mill producing the rolls corresponding to the right side of the graph 66.

While the invention has been described with respect to certain preferred embodiments, it is apparent that various changes can be made without departing from the scope of the invention as defined by the appended claims.

We claim:

1. A testing apparatus for determining hardness characteristics of an array of paper, said testing apparatus comprising:

a tester including a housing, impact means mounted in the housing for impacting the paper being tested, hardness measuring means coupled to the impact means for generating signals indicative of hardness based upon the impact of the paper by the impact means, traversal means mounted to the housing for permitting movement of the tester across the paper, and position sensing means mounted to the housing for generating signals identifying the position of the impact means on the paper at each impact by the impact means, wherein said traversal means comprises an array of wheels spaced from the impact means and the position sensing means;

computer means operatively connected to the hardness measuring means and the position sensing means for receiving signals therefrom and for calculating hardness at each of plural impacted positions across the paper being tested; and output means operatively connected to the computer for providing output data indicative of the hardness of the paper being tested at each of the plural impacted positions across the paper.

2. An apparatus as in claim 1, wherein the array of wheels comprises at least three wheels disposed to rotate around parallel axes, the wheels being disposed with respect to the impact means to enable support of the tester when the impact means is adjacent an edge of the paper being tested.

3. A testing apparatus for determining hardness characteristics of an array of paper, said testing apparatus comprising:

a tester including a housing, impact means mounted in the housing for impacting the paper being tested, hardness measuring means coupled to the impact means for generating signals indicative of hardness based upon the impact of the paper by the impact means, traversal means mounted to the housing for permitting movement of the tester across the paper, and position sensing means mounted to the housing for generating signals identifying the position of the impact means on the paper at each impact by the impact means, the position sensing means comprising an encoder wheel of generally frustoconical configuration and having a major diameter portion disposed for rolling contact with the paper being tested;

computer means operatively connected to the hardness measuring means and the position sensing means for receiving signals therefrom and for calculating hardness at each of plural impacted positions across the paper being tested; and output means operatively connected to the computer for providing output data indicative of the hardness of the paper being tested at each of the plural impacted positions across the paper.

* * * * *